US009844664B2

(12) United States Patent
McEvoy et al.

(10) Patent No.: US 9,844,664 B2
(45) Date of Patent: Dec. 19, 2017

(54) INTERVENTIONAL MEDICAL SYSTEMS, CATHETERS, AND SUBASSEMBLIES

(71) Applicant: Medtronic, Inc., Minneapolis, MN (US)

(72) Inventors: Francis D McEvoy, Laois (IE); Brendan P Geraghty, Galway (IE); Paula McDonnell, Galway (IE); Pat McHugh, Ballyhaunis co. Mayo (IE); Colin W Meade, Westmeath (IE); Sean Ward, Dublin (IE); Rónán Wood, Galway (IE); Kealan E O'Carroll, Galway (IE); Tomas K Kelly, Galway (IE); Gwenda Francis, Galway (IE)

(73) Assignee: Medtronic, Inc., Minneapolis, MN (US)

( * ) Notice: Subject to any disclaimer, the term of this patent is extended or adjusted under 35 U.S.C. 154(b) by 326 days.

(21) Appl. No.: 14/880,371

(22) Filed: Oct. 12, 2015

(65) Prior Publication Data
US 2017/0100582 A1  Apr. 13, 2017

(51) Int. Cl.
*A61N 1/05* (2006.01)
*A61N 1/362* (2006.01)
(Continued)

(52) U.S. Cl.
CPC ........... *A61N 1/0573* (2013.01); *A61N 1/362* (2013.01); *A61N 1/3756* (2013.01);
(Continued)

(58) Field of Classification Search
CPC ................ A61N 1/0573; A61N 1/3756; A61N 1/37205; A61N 1/362; A61N 2001/0578;
(Continued)

(56) References Cited

U.S. PATENT DOCUMENTS 2,114,695 A   4/1938 Anderson
4,655,219 A   4/1987 Petruzzi
(Continued)

FOREIGN PATENT DOCUMENTS

WO   2004028348 A2   4/2004

OTHER PUBLICATIONS (PCT/US2016/038490) PCT Notification of Transmittal of the International Search Report and the Written Opinion of the International Searching Authority, dated Sep. 21, 2016, 10 pages.

*Primary Examiner* — Julian W Woo

(57) ABSTRACT

An engagement subassembly of a catheter, for retrieving an implanted medical device, may include at least three segments or, alternately, capture members being spring biased outward from a longitudinal axis of the subassembly, wherein a device receptacle of the catheter forces the capture members/segments, against the spring bias thereof, toward the axis. Each capture member includes a spring-biased wire and a grip, which is located between proximal and distal portions of the corresponding wire, and which is configured to interlock within a gap between a device attachment feature and housing; a length of each wire distal portion may be approximately equal to that of the device housing. An interlocking edge of each segment interlocks within the gap between the attachment feature and housing, when a distal-facing surface of each segment, which tapers outward from the axis in a distal direction, comes into confronting engagement with the device housing.

19 Claims, 11 Drawing Sheets

(51) Int. Cl.
    *A61N 1/372*     (2006.01)
    *A61N 1/375*     (2006.01)
    *A61M 25/00*     (2006.01)
    *A61B 17/22*     (2006.01)

(52) U.S. Cl.
    CPC   *A61N 1/37205* (2013.01); *A61B 2017/22035* (2013.01); *A61M 25/0074* (2013.01); *A61M 2025/0004* (2013.01); *A61N 2001/0578* (2013.01)

(58) Field of Classification Search
    CPC ...... A61M 2025/0004; A61M 25/0074; A61B 2017/22035
    See application file for complete search history.

(56) References Cited

U.S. PATENT DOCUMENTS

| | | |
|---|---|---|
| 5,417,697 A | 5/1995 | Wilk et al. |
| 5,476,510 A | 12/1995 | Eberhardt et al. |
| 5,902,331 A | 5/1999 | Bonner et al. |
| 6,010,526 A | 1/2000 | Sandstrom et al. |
| 6,156,055 A | 12/2000 | Ravenscroft |
| 6,187,016 B1 | 2/2001 | Hedges et al. |
| 6,506,205 B2 | 1/2003 | Goldberg et al. |
| 6,846,317 B1 | 1/2005 | Nigon |
| 6,953,473 B2 | 10/2005 | Porter |
| 7,033,376 B2 | 4/2006 | Tsukernik |
| 7,092,765 B2 | 8/2006 | Geske et al. |
| 7,323,003 B2 | 1/2008 | Lowe |
| 7,473,266 B2 | 1/2009 | Glaser |
| 7,676,268 B2 | 3/2010 | Hettrick et al. |
| 7,801,626 B2 | 9/2010 | Moser |
| 8,025,668 B2 | 9/2011 | McCartney |
| 8,364,280 B2 | 1/2013 | Marnfeldt et al. |
| 9,480,850 B2 * | 11/2016 | Schmidt ............... A61N 1/3756 |
| 2005/0267555 A1 | 12/2005 | Marnfeldt et al. |
| 2008/0283066 A1 | 11/2008 | Delgado et al. |
| 2012/0165827 A1 | 6/2012 | Khairkhahan et al. |
| 2013/0116704 A1 | 5/2013 | Geistert |
| 2015/0051609 A1 | 2/2015 | Schmidt et al. |
| 2015/0051611 A1 | 2/2015 | Schmidt et al. |
| 2015/0094668 A1 | 4/2015 | Wood et al. |

\* cited by examiner

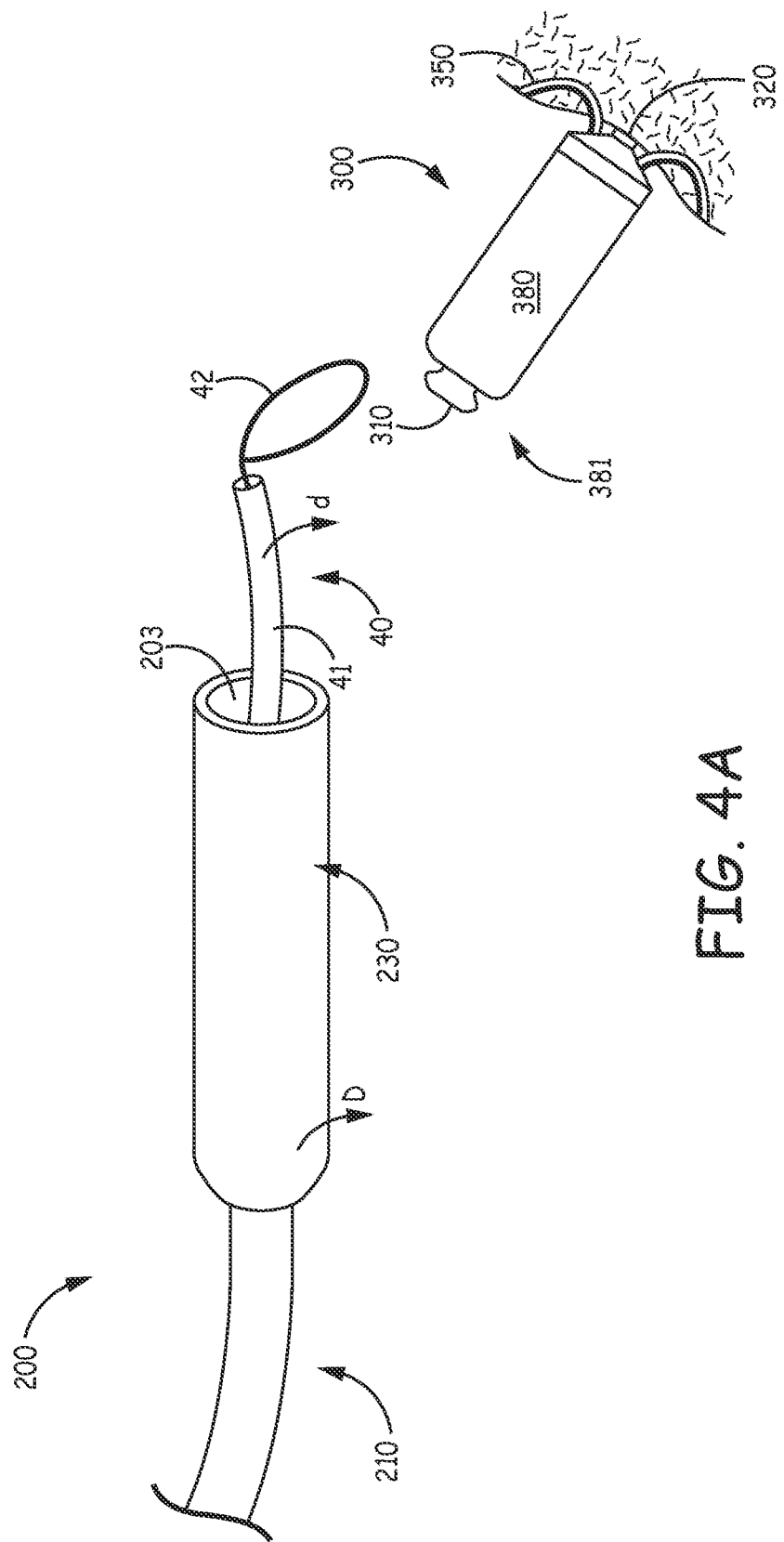

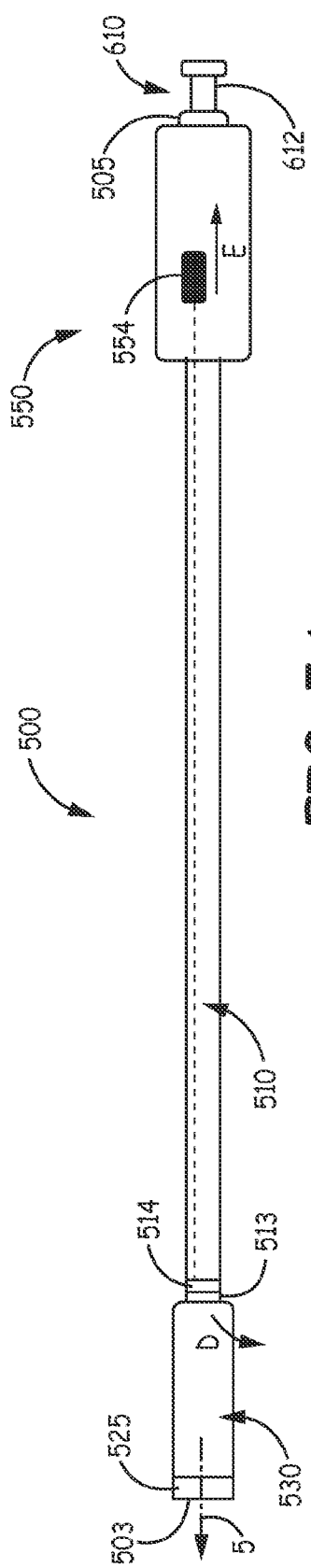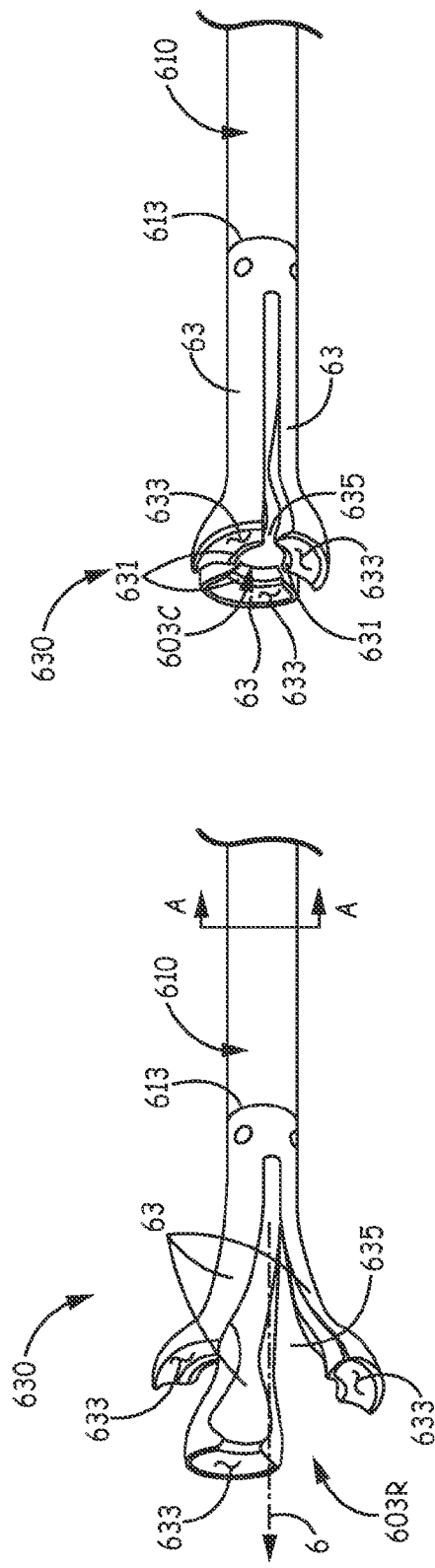
FIG. 5A
FIG. 5B
FIG. 5C

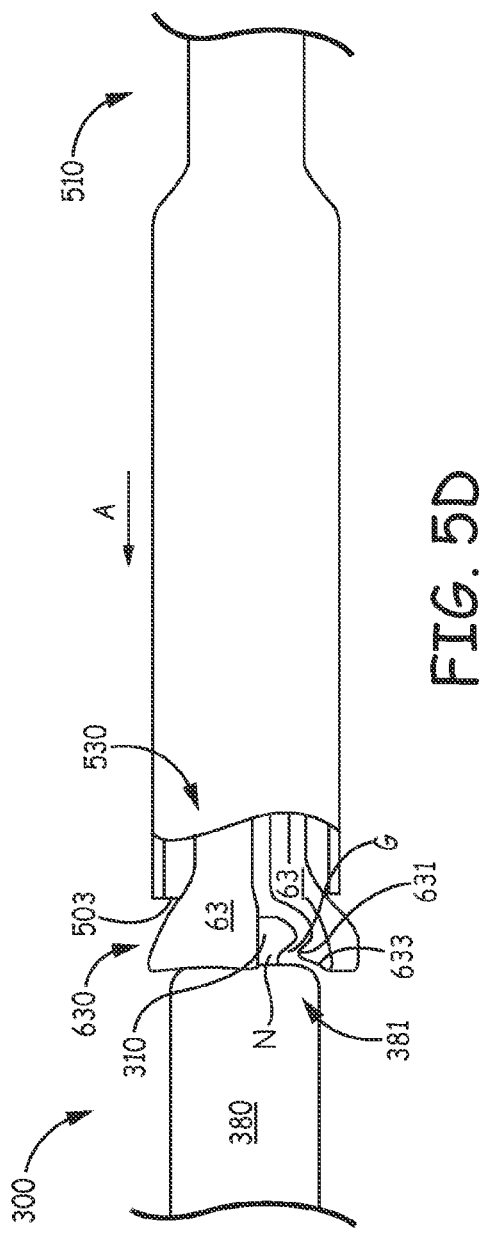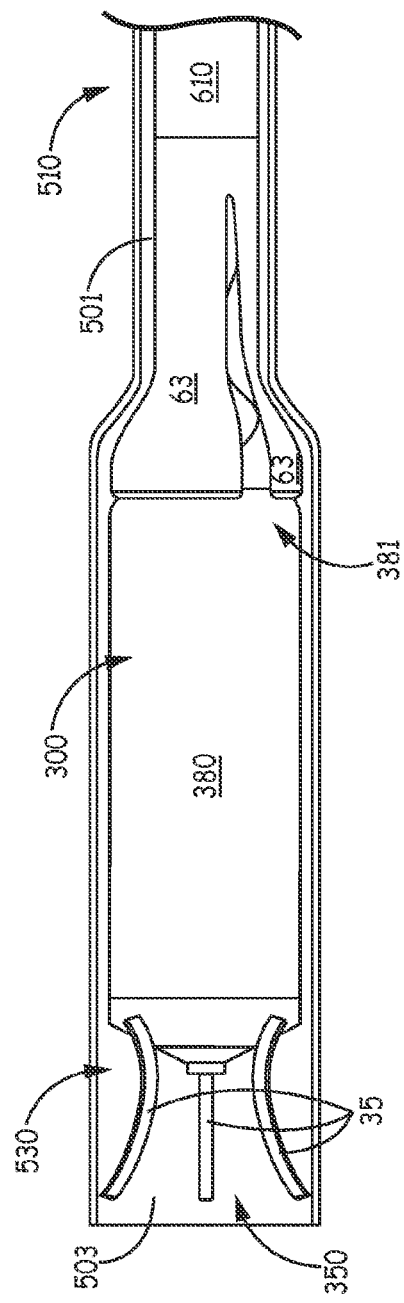

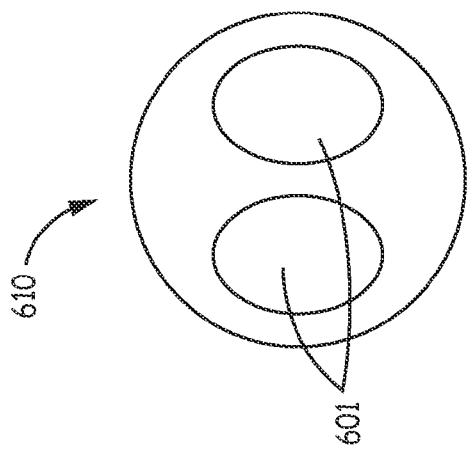
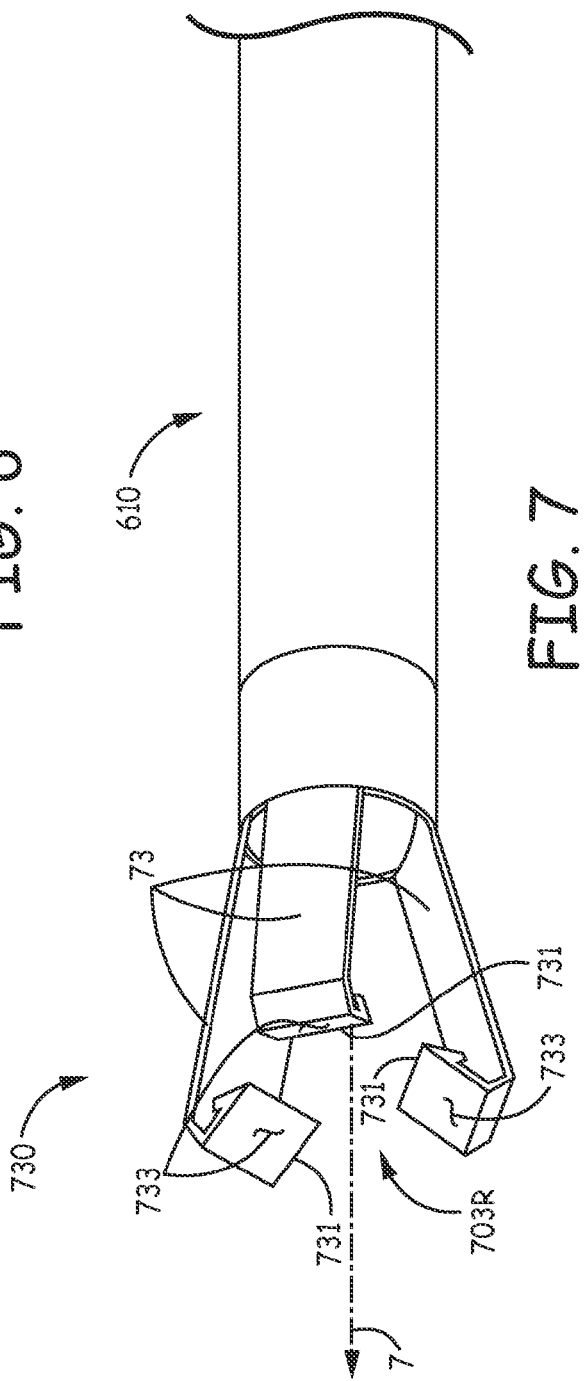

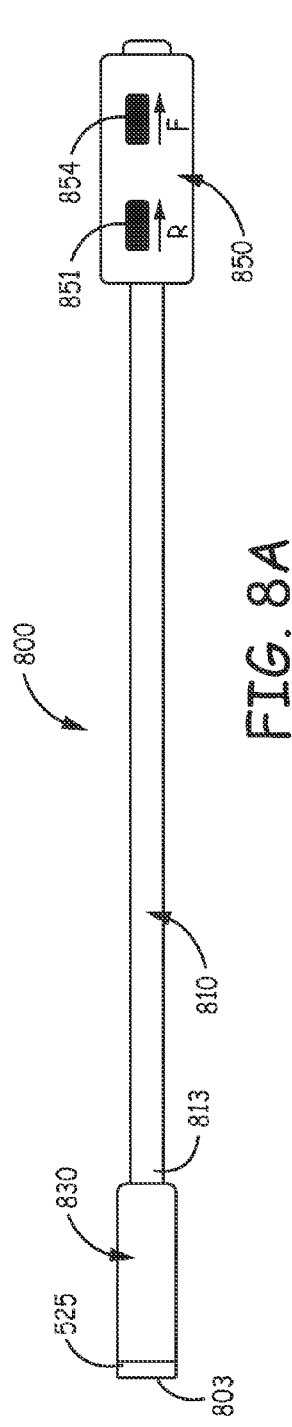
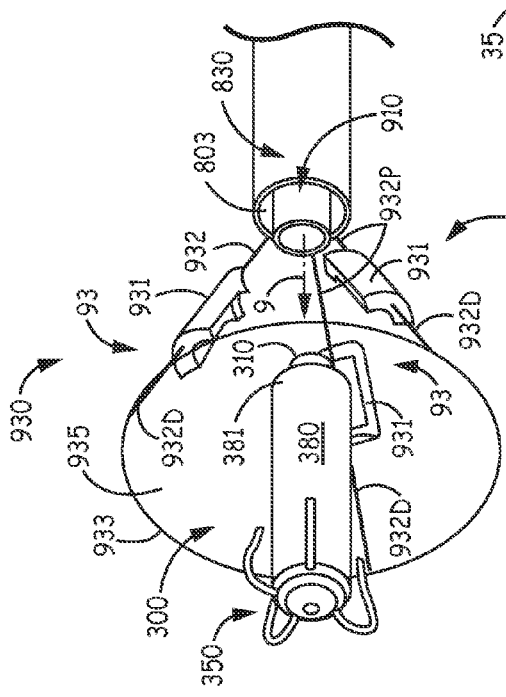
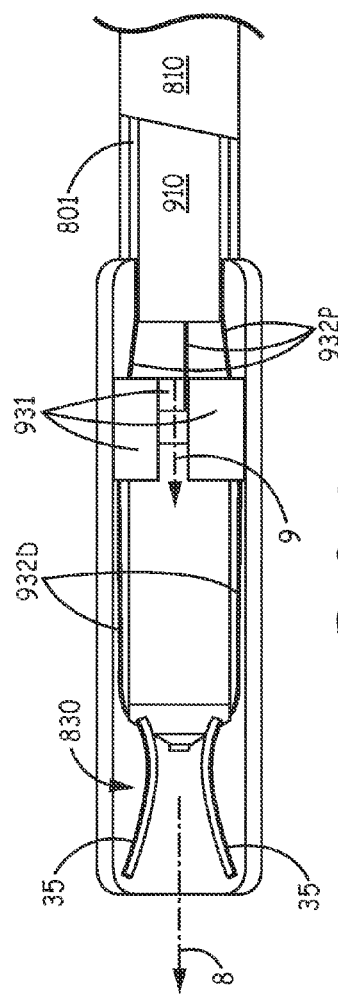
FIG. 8A
FIG. 8B
FIG. 8C

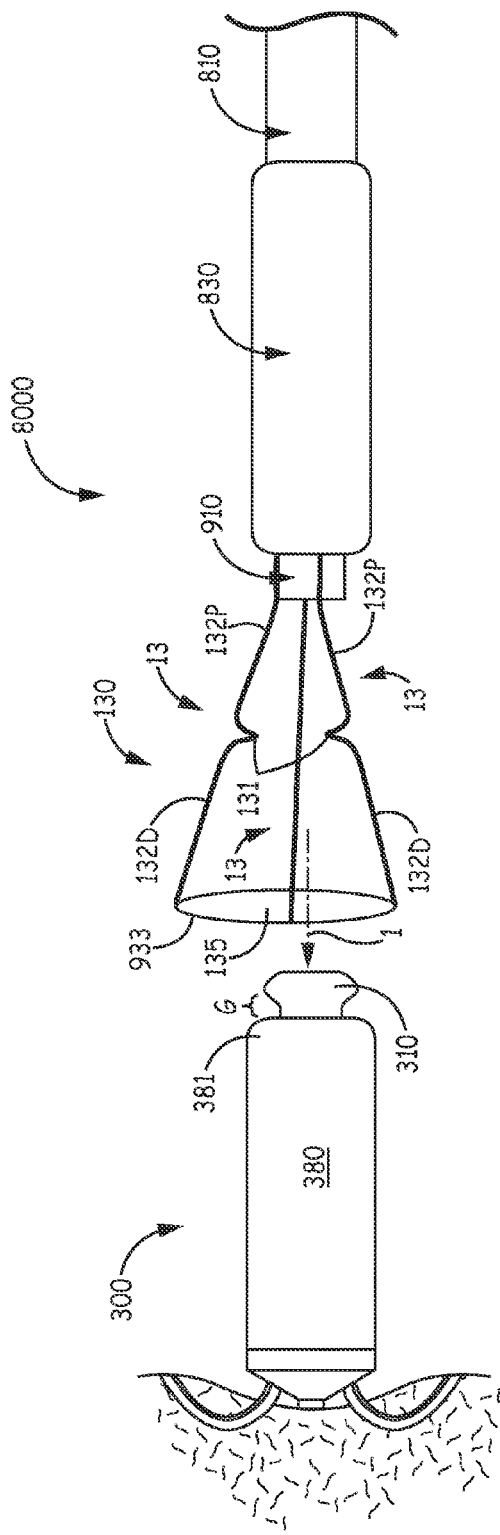
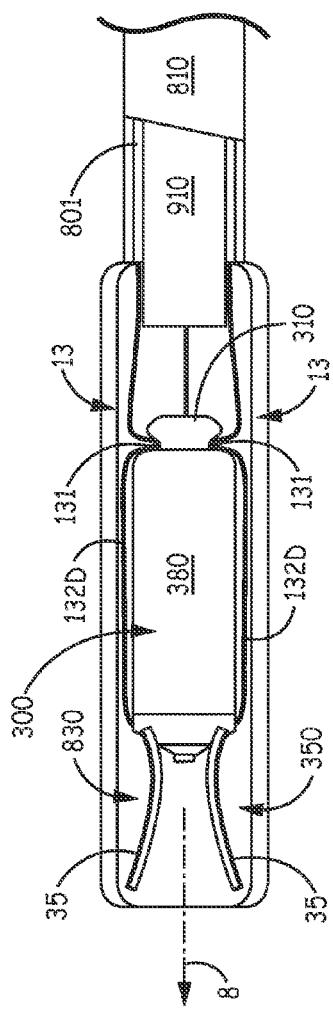
FIG. 9A
FIG. 9B

INTERVENTIONAL MEDICAL SYSTEMS, CATHETERS, AND SUBASSEMBLIES

FIELD OF THE DISCLOSURE

The present disclosure pertains to interventional medical systems, and more particularly to systems, catheters and subassemblies that are useful for retrieving medical devices from implant sites.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical and/or MRI compatibility issues, which are sometimes associated with elongate lead wires and well known to those skilled in the art, have motivated the development of implantable cardiac pacing devices that are wholly contained within a relatively compact package, the entirety of which is configured for implant in close proximity to the pacing site. FIG. 1 is a schematic diagram that shows potential cardiac implant sites for such a device, for example, within an appendage 102 of a right atrium RA, within a coronary vein CV (via a coronary sinus ostium CSOS), or in proximity to an apex 103 of a right ventricle RV, for example, as shown in FIG. 2.

FIG. 2 shows an implantable medical device 300 having been implanted by an operator using a catheter 200, for example, like the tool described in the commonly assigned United States Patent Application US 2015/0094668, wherein the operator advanced tool 200 into the right heart through the inferior vena cava IVC, for example, from a femoral vein access site, and then deployed device 300 from a device receptacle 230 of catheter 200. In some cases, when it may be necessary to retrieve the implanted device, the operator can employ catheter 200 to do so, but new and improved catheters would increase the ease and efficiency of retrieval.

SUMMARY

Catheters of interventional medical systems, disclosed herein, have inner assemblies that include engagement subassemblies configured to retrieve implantable medical devices from an implant site. According to some embodiments of such a catheter, an engagement subassembly is coupled to a distal end of a shaft of the inner assembly, wherein the shaft is in sliding engagement with a longitudinally extending lumen of a shaft of an outer assembly of the catheter, and the engagement subassembly is in sliding engagement with a device receptacle of the outer assembly. The device receptacle of the outer assembly is joined to a distal end of the outer assembly shaft, being in fluid communication with the lumen thereof, is sized to contain the medical device therein, and has a distal-most opening that allows passage of the device therethrough. The engagement subassembly may include at least three segments or, alternately, at least three capture members arranged around a longitudinal axis of the subassembly and being spring biased outward from the longitudinal axis, wherein the device receptacle of the catheter outer assembly forces the capture members/segments, against the spring bias thereof, toward the longitudinal axis, which is approximately aligned with a longitudinal axis of the device receptacle when the engagement subassembly is contained therein.

In some embodiments of the engagement subassembly, each capture member thereof includes an elongate spring-biased wire and a grip that is located between proximal and distal portions of the corresponding spring-biased wire, wherein each grip is configured to interlock within a gap between an attachment feature of the device and a proximal end of a housing of the device, when the device receptacle of the catheter outer assembly forces the capture members, against the spring-bias thereof, toward the longitudinal axis of the engagement subassembly. Furthermore, a length of the distal portion of each spring-biased wire may be approximately equal to a length of the device housing, and extends alongside the device housing, when the grip of each capture member interlocks within the gap between the device attachment feature and the proximal end of the device housing. The engagement subassembly may further include a pull band and an elongate pull wire coupled thereto, for deflection of the shaft of the catheter inner assembly, wherein the pull wire extends along a length of the inner assembly shaft, the proximal portion of the spring-biased wire of each capture member is coupled to the pull band, and the pull band is mounted in the distal end of the inner assembly shaft.

In some alternate embodiments of the engagement subassembly, each segment thereof has a distal-facing surface tapering outward from the longitudinal axis of the engagement subassembly in a distal direction, and an interlocking edge terminating the distal-facing surface at a proximal end thereof, wherein the distal-facing surfaces of the segments, together, define a distal-most opening into the interior of the engagement subassembly, and are oriented for confronting engagement with the proximal end of the device housing, when the device receptacle of the catheter outer assembly forces the segments, against the spring-bias thereof, toward the longitudinal axis of the engagement subassembly. Furthermore, the interlocking edge of each segment is configured to interlock within the gap between the device attachment feature and the proximal end of the device housing, when the distal-facing surface of each segment is in confronting engagement with the proximal end of the device housing.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIGS. 4A-B are schematics depicting a difficulty that may be encountered by an operator when attempting to retrieve the medical device from an implant site;

FIG. 5A is a plan view of a catheter, which may be included in the interventional medical system, according to some embodiments;

FIGS. 5B-C are perspective views of an engagement subassembly, which may be part of an inner assembly of the catheter of FIG. 5A, according to some embodiments;

FIGS. 5D-E are plan views, with partial cross-sections, of a portion of the interventional medical system that includes the device of FIG. 3 and the catheter of FIGS. 5A-C, according to some embodiments;

FIG. 6 is a cross-section view through section line A-A of FIG. 5B, according to some embodiments;

FIG. 7 is a perspective view of an engagement subassembly, according to some alternate embodiments;

FIG. 8A is a plan view of a catheter, according to some alternate embodiments;

FIG. 8B is a perspective view of a portion of an interventional medical system that includes the device of FIG. 3 and the catheter of FIG. 8A, according to some embodiments;

FIG. 8C is a plan view, with partial cross-section, of the portion of the system in another condition than that shown in FIG. 8B, according to some embodiments;

FIG. 9A is a plan view of a portion of an interventional medical system, according to yet further embodiments; and FIG. 9B is another plan view of the system, with a partial cross-section.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives. As used in this disclosure, the term "approximately," as used in this specification and appended claims, refers to plus or minus 5% of the stated value.

Figure 3:
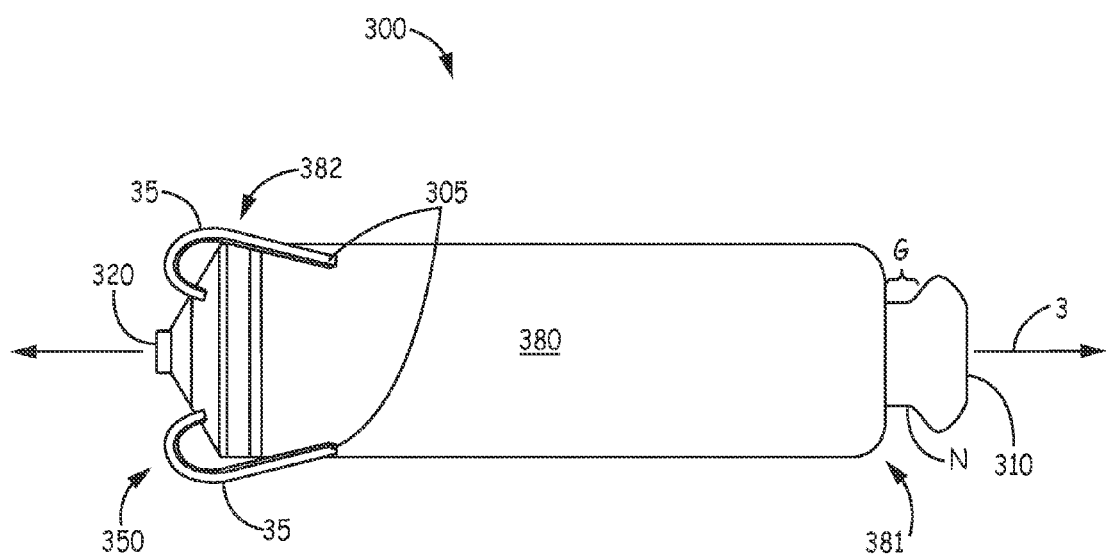
FIG. 3 is a plan view of the exemplary relatively compact implantable medical device, which may be part of an interventional medical system, according to some embodiments.

FIG. 3 is a plan view of exemplary relatively compact implantable medical device 300, which may be part of an interventional medical system, for example, according to some embodiments described below. FIG. 3 illustrates device 300 including a hermetically sealed housing 380 extending from a proximal end 381 thereof to a distal end 382 thereof and along a longitudinal axis 3. Device 300 further includes an electrode 320 and a fixation member 350, both mounted in proximity to distal end 382 of housing 380, and an electronic controller (not shown), for example, a pulse generator and an associated power supply, contained in housing 380, wherein electrode 320 is electrically coupled to the controller via a hermetically sealed feedthrough assembly (not shown) such as is known in the art. Housing 380, for example, formed from a biocompatible and biostable metal such as titanium, may be overlaid with an insulative layer, for example, medical grade polyurethane, parylene, or silicone, and, although not shown, device 300 may include another electrode, for example, formed by removing a portion of the insulative layer to expose the metallic surface of housing 380. The other electrode may function in conjunction with electrode 320 for bipolar pacing and sensing, when fixation member 350 secures electrode 320 in intimate tissue contact at a target implant site. FIG. 3 further illustrates device 300 including an attachment feature 310 joined to proximal end 381 of housing 380 and protruding proximally therefrom. Attachment feature 310 is both useful for maintaining control over device 300, for example, with a tether member attached thereto, when deploying device 300 to an implant site, for example, as described in the aforementioned commonly-assigned U.S. Patent Application US 2015/0094668, and for retrieving device 300 from the implant site, as described below. Feature 310 is shown including a necked-in portion N that defines a gap G between feature 310 and housing proximal end 381.

With further reference to FIG. 3, device fixation member 350 includes a plurality of fingers 35 spaced apart from one another around a perimeter of device housing distal end 382. Although only two fingers 35 of fixation member 350 are shown in FIG. 3, fixation member 350 may include as many as eight fingers 35. According to an exemplary embodiment, fixation fingers 35 are integrally formed with one another, having been cut from Nitinol tubing, according to methods known in the art. After cutting the Nitinol tubing, fingers 35 may be shaped by bending and holding fingers 35 in the illustrated curvature while heat treating, according to methods known to those skilled in the art. Fixation member 350 may be mounted to distal end 382 of device housing 380, for example, in a manner similar to that described for a fixation component 102 in a commonly assigned United States Patent Application 2012/0172690, which description is hereby incorporated by reference. The super-elastic nature of Nitinol allows fingers 35 to elastically deform between a relaxed condition, which is shown, and an extended condition, in which a free end 305 of each finger extends distally away from distal end 382 of device housing 380, for example, as shown in FIGS. 8C and 9B.

Figure 2:
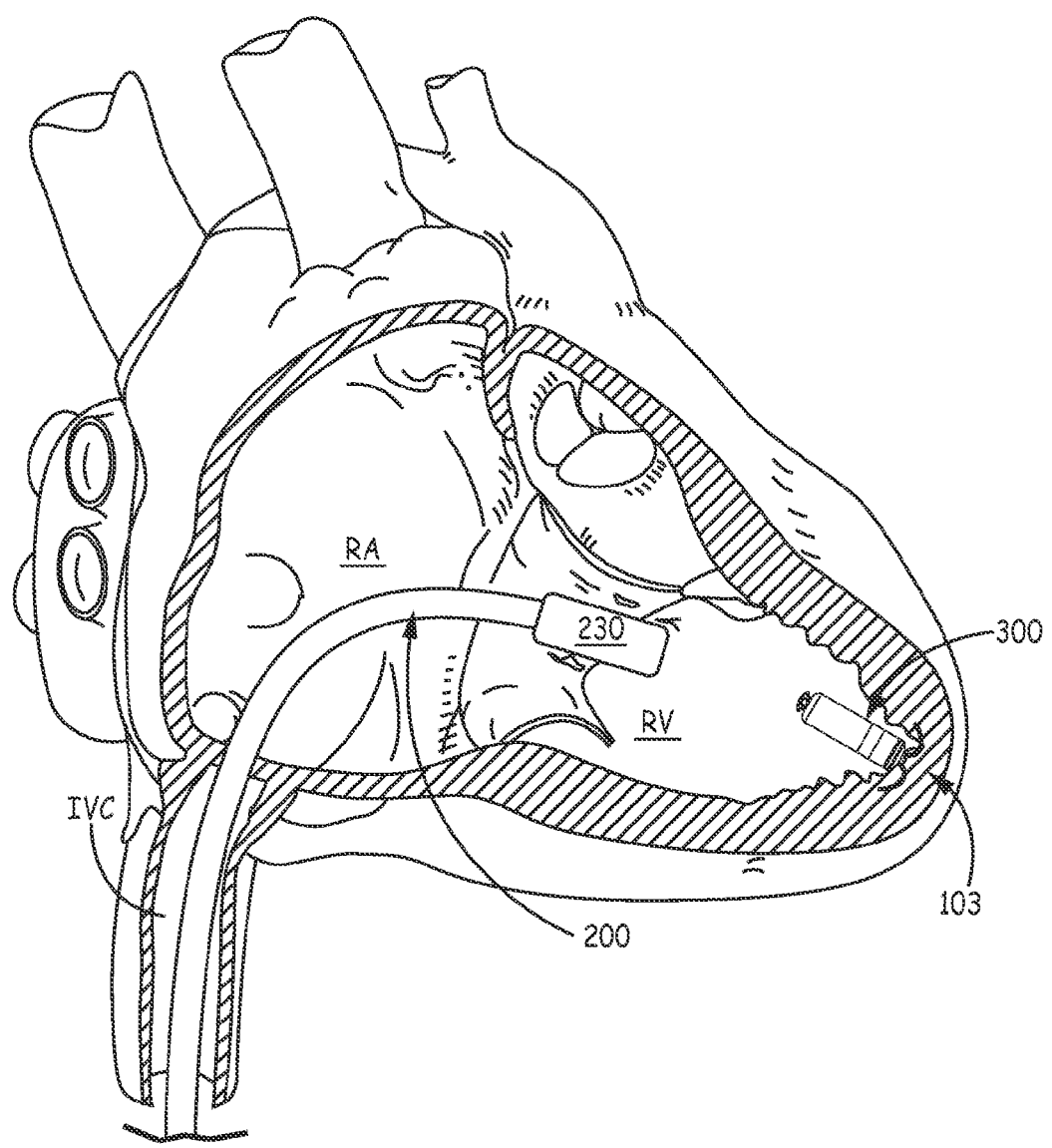
FIG. 2 is a schematic showing an exemplary relatively compact implantable medical device having been delivered from a catheter to an implant site.
Figure 4B:
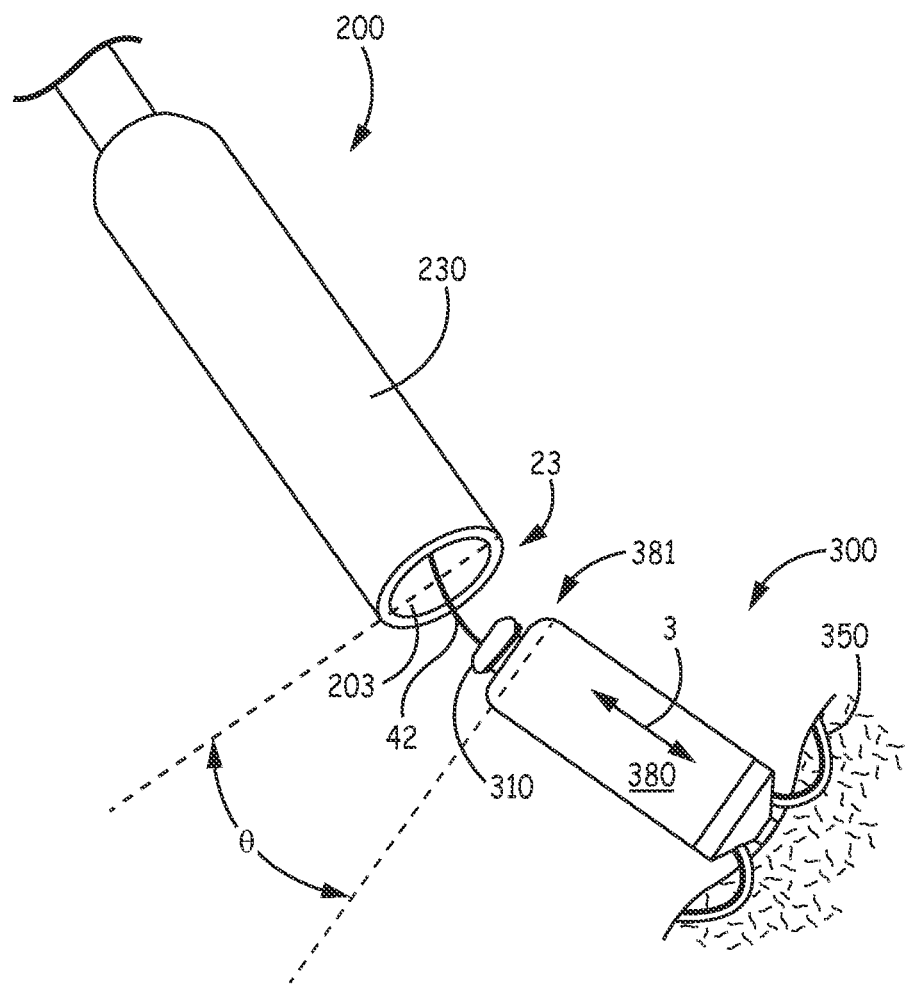

FIGS. 4A-B are schematics depicting a difficulty that may be encountered by an operator when attempting to retrieve medical device 300 from an implant site, for example, the site in proximity to an apex 103 of a right ventricle RV shown in FIG. 2. FIG. 4A illustrates device receptacle 230 of catheter 200 having been advanced to the implant site, and a device retrieval tool 40 having been passed out through a distal-most opening 203 of receptacle 230. Retrieval tool 40 includes elongate snare member 42, which extends within a shaft 41 of tool 40, and which is slideably engaged within shaft 41 to open and close a loop thereof. Snare member 42 is shown deployed to snare device attachment feature 310, and the operator may deflect, per arrow d, shaft 41, via a steering assembly thereof, to maneuver the deployed snare member 42 into position around attachment feature 310.

Figure 1:
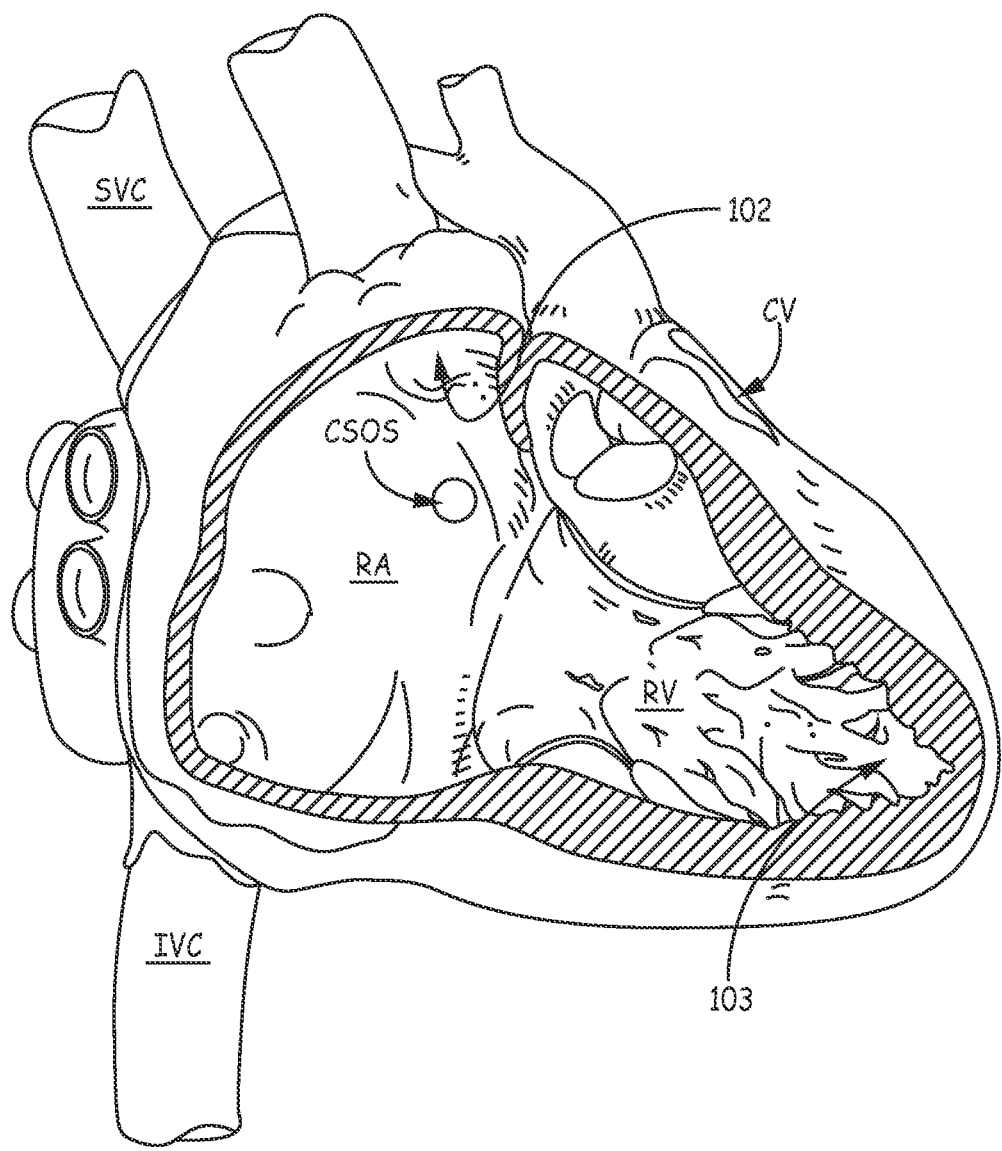
FIG. 1 is a schematic diagram showing potential implant sites for a relatively compact implantable medical device.

Once the operator has snared attachment feature 310, the operator may advance catheter 200 over retrieval tool 40 until opening 203 is brought into proximity with device housing proximal end 381, as shown in FIG. 4B. FIG. 4B illustrates an angle θ that corresponds to a misalignment of a plane of distal-most opening 203 of receptacle 230 and a plane of proximal end 381 (approximately orthogonal to longitudinal axis 3 of device 300). The misalignment will likely cause a distal-most edge 23 of receptacle 230 to catch on an edge of device proximal end 381, so that the operator may find it difficult to advance receptacle 230 over the snared device 300, or to pull the snared device 300 into receptacle 230. The angle of misalignment θ encountered in some cardiac implant sites, for example, in appendage 102 of the right atrium RA, or near apex 103 of the right ventricle RV (FIG. 1), may be as great as 45 degrees.

FIG. 5A is a plan view of a catheter 500, which may be included in an interventional medical system, according to some embodiments. FIG. 5A illustrates an outer assembly of catheter 500 including an elongate shaft 510, a handle 550 joined to a proximal end of shaft 510, and a device receptacle 530 joined to a distal end 513 of shaft 510. According to the illustrated embodiment, shaft 510 includes a longitudinally extending lumen 501 (seen in FIG. 5E), with which device receptacle 530 is in fluid communication, wherein receptacle 530 is sized to contain medical device 300 (also seen in FIG. 5E) and has a distal-most opening 503 that allows passage of device 300 therethrough. FIG. 5A further illustrates a proximal end 612 of an elongate shaft 610 of an inner assembly of catheter 500 extending from a proximal end of handle 550. Shaft 610 extends within lumen 501, being in sliding engagement therewith, and a distal end 613 of shaft is coupled to an engagement subassembly 630 of the inner assembly of catheter 500, for example, as shown in FIGS. 5B-C, wherein engagement subassembly 630 is in sliding engagement with receptacle 530 of the outer assembly of catheter 500, for example, as shown in FIGS. 5D-E, so that subassembly 630 can be advanced out through distal-most opening 503 to retrieve device 300 from an implant site.

FIGS. 5B-C are perspective views of engagement subassembly 630 separate from catheter 500, wherein FIG. 5B shows subassembly 630 in a relaxed, or spring-biased, condition, and FIG. 5C shows subassembly 630 in a compressed condition, according to some embodiments. FIG. 5B illustrates subassembly 630 including at least three longitudinally extending segments 63 arranged around, and spring biased outward from, a longitudinal axis 6 of engagement subassembly 630. FIG. 5C illustrates segments 63 of subassembly 630 forced, against the spring-bias thereof, toward axis 6, which would be the case when subassembly 630 is contained within receptacle 530 of the outer assembly of catheter 500. Note that, when engagement subassembly 630 is contained within device receptacle 530, longitudinal axis 6 is approximately aligned with a longitudinal axis 5 of receptacle 530 (FIG. 5A). FIGS. 5B-C further illustrate each segment 63 including a distal-facing surface 633 tapering outward from axis 6 in a distal direction, wherein distal-facing surfaces 633 define a distal-most opening 603R, 603C into an interior 635 of engagement subassembly 630 (603R in the relaxed condition, and 603C in the compressed condition). According to the illustrated embodiment, each distal-facing surface 633 is oriented for confronting engagement with housing proximal end 381 of device 300, when device receptacle 530 forces segments 63, against the spring-bias thereof, toward axis 6, for example, as illustrated in FIGS. 5D-E. Furthermore, a proximal end of each distal-facing surface 633 is shown being terminated by an interlocking edge 631 that interlocks within gap G between device attachment feature 310 and housing proximal end 381, when distal-facing surface 633 of each segment 63 is in confronting engagement with housing proximal end 381.

With further reference to FIGS. 5A-B, when an operator has positioned device receptacle 530 of the outer assembly of catheter 500 in proximity to implanted medical device 300, for example, at implant site 103 of FIG. 2, the operator may move the inner assembly of catheter 500, relative to the outer assembly, to advance engagement subassembly 630 out from distal-most opening 503. Once outside the constraint of receptacle 530, segments 63 open outward, according to the spring-bias thereof, as shown in FIG. 5B, to provide the enlarged opening 603R into interior 635 of engagement subassembly 630 that allows the operator to initially engage device attachment feature 310, for example, to overcome the alignment difficulty described above in conjunction with FIGS. 4A-B. With reference to FIG. 5D, once segments 63 surround device attachment feature 310, the outer assembly of catheter 500 can be advanced, per arrow A, over engagement subassembly 630, which forces segments 63 thereof together around device attachment feature 310 so that distal-facing surfaces 633 come into confronting engagement with proximal end 381 of device housing 380 and interlocking edges 631 interlock within the aforementioned gap G. Although not shown, the system may also include an outer sheath, with which catheter 500 is in sliding engagement, and which includes a cutting distal-most edge. If the implanted device 300 has become encapsulated with tissue, such a sheath may be advanced over catheter 500, for example, after engagement subassembly engages with device attachment feature 310, to cut through the encapsulating tissue.

FIG. 5D further illustrates each distal-facing surface 633 having a curved contour that conforms to a curved contour of device housing proximal end 381, and interlocking edges 631 together defining a circular perimeter of distal-most opening 603C (best seen in FIG. 5C) that surrounds necked-in portion N of attachment feature 310 when surfaces 633 come into confronting engagement with housing proximal end 381. When receptacle 530 fully contains engagement subassembly 630 so that segments 63 have fully closed around device attachment feature 310, the operator can apply a pull force to the inner assembly, along shaft 610, to disengage device fixation member 350 from the implant site and bring device 300 into receptacle 530, so that fingers 35 of fixation member 350 are held in the extended condition, as illustrated in FIG. 5E.

With reference back to FIG. 5A, in some exemplary embodiments, outer assembly shaft 510 of catheter 500, for example, extending over a length of approximately 100 cm, may be formed by a stainless steel braid-reinforced medical grade polymer, for example, one or more appropriate grades of polyether block amide, which are arranged for decreasing stiffness from handle 550 to shaft distal end 513 (e.g., PEBAX® 3533, 6333, 4033, and 7233), and lumen 501 may have a diameter of approximately 0.154 inch (3.9 mm). Device receptacle 530, for example, having an inner diameter of approximately 0.3 inch (7.6 mm), and a length of at least 31 millimeters, may be formed from a medical grade polyether block amide (e.g., PEBAX® 7233 SA-01), with which a radiopaque filler may be blended, or to which a radiopaque marker 525 (e.g., Tungsten-filled Vestamid®) is bonded, either according to methods known to those skilled in the art. With further reference to FIG. 5A, catheter 500 may include a steering assembly for deflecting distal end 513 of shaft 510, per arrow D, wherein the steering assembly includes a pull band 514, which is mounted in shaft distal end 513, an elongate pull wire (dashed line), which extends along a length of shaft 510, and an actuator 554, which is mounted to handle 550. A distal end of the pull wire may be coupled to pull band 514, for example, by a weld or a crimp joint, and a proximal end of the pull wire may be coupled to actuator 554, for example, by a crimp joint, such that moving actuator per arrow E causes the pull wire to deflect shaft 510 per arrow D, which may be useful in navigating catheter 500 into proximity with the implanted device 300.

With respect to the inner assembly of catheter 500, according to exemplary embodiments, shaft 610 may be formed from a stainless steel braid-reinforced medical grade polymer, for example, one or more appropriate grades of polyether block amide, which are arranged for decreasing stiffness from a proximal end of shaft 610 to distal end 613 (e.g., PEBAX® 3533, 6333, 4033, and 7233), and shaft 610 may include a fluoropolymer liner, for example, PTFE. Engagement subassembly 630 may be formed from a medical grade Nitinol, for example, having been cut from Nitinol tubing and then heat treated to set the spring-biased condition shown in FIG. 5B; alternately, subassembly 630 may be formed by laser sintering a medical grade Stainless Steel. A diameter of compressed opening 603C may be approximately 3 mm, and a diameter of enlarged opening 603R may be approximately 7 mm. Engagement subassembly 630 may be coupled to shaft distal end 613 via any suitable bonding method in combination with an interlocking fit, according to methods known in the art.

Inner assembly shaft 610 may include one or more lumens 601 (FIG. 6) in fluid communication with interior 635 of engagement subassembly 630 and extending longitudinally from proximal end 612 to distal end 613. According to some embodiments one of lumens 610 is configured to receive, in sliding engagement therewith, an optional snare tool, for example, like tool 40 described above, which may be employed in conjunction with engagement subassembly 630 to retrieve implanted device 300. FIG. 6 is a cross-section view through section line A-A of FIG. 5B, according to some embodiments, in which inner assembly shaft 610 includes at least two lumens 601 to accommodate a tether member for device 300. If catheter 500 is employed to deploy device 300 at the implant site, as well as to subsequently retrieve device 300, as described above, the tether member may be looped around device attachment member 310 and threaded through lumens 601 to temporarily secure device 300 to catheter 500, for example, as described in the aforementioned commonly assigned U.S. Patent Application US 2015/0094668.

FIG. 7 is a perspective view of an engagement subassembly 730, according to some alternate embodiments, which may be substituted for subassembly 630 in catheter 500. FIG. 7 illustrates engagement subassembly 730 including at least three longitudinally extending segments 73 arranged around, and being spring biased outward from, a longitudinal axis 7 of engagement subassembly 730, wherein each segment 73 includes a distal-facing surface 733 tapering outward from axis 6 in a distal direction, and distal-facing surfaces 733 define a distal-most opening 703 into an interior 735 of engagement subassembly 730. Like engagement subassembly 630, a proximal end of each distal-facing surface 733 is terminated by an interlocking edge 731, but distal-facing surfaces 733 are relatively flat rather than having the curved contour defined for distal-facing surfaces 633 of subassembly 630. FIG. 7 shows subassembly 730 in a relaxed, or spring-biased, condition, outside the constraint of device receptacle 530 of the outer assembly of catheter 500, but when segments 73 are forced, against the spring-bias thereof, toward axis 7, for example, by receptacle 530 of the outer assembly of catheter 500, distal-most opening 703 becomes compressed, and longitudinal axis 7 is approximately aligned with longitudinal axis 5 of receptacle 530. According to the illustrated embodiment, each distal-facing surface 733 is oriented for confronting engagement with device housing proximal end 381, when device receptacle 530 of catheter 500 forces segments 73, against the spring-bias thereof, toward axis 7, for example, as described above for subassembly 633, in conjunction with FIGS. 5D-E. Furthermore, each interlocking edge 731 interlocks within gap G between device attachment feature 310 and housing proximal end 381, when distal-facing surface 733 of each segment 73 is in confronting engagement with housing proximal end 381.

FIG. 8A is a plan view of a catheter 800, according to some alternate embodiments. FIG. 8A illustrates an outer assembly of catheter 800 including an elongate shaft 810, a handle 850 joined to a proximal end of shaft 810, and a device receptacle 830 joined to a distal end 813 of shaft 810. Shaft 810 and receptacle 830 may be constructed like the above-described exemplary embodiment of the outer assembly of catheter 500. FIG. 8A further illustrates handle 850 including a control member 851, which is coupled to the proximal end of shaft 810, wherein control member 851 advances and retracts the outer assembly of catheter 800 relative to an inner assembly of catheter 800. The inner assembly includes a shaft 910 that extends within a longitudinally extending lumen 801 of outer assembly shaft 810, and an engagement subassembly 930, which is coupled to a distal end of shaft 910, for example, as seen in FIGS. 8B-C.

FIGS. 8B-C are a perspective view and a plan view, with partial cross-section, respectively, of a distal portion of catheter 800 together with medical device 300. Device receptacle 830 is in fluid communication with shaft lumen 801, and engagement subassembly 930 is in sliding engagement with receptacle 830, so that, when the outer assembly is retracted relative to the inner assembly, per arrow R (FIG. 8A), subassembly 930 is released to a relaxed, or spring-biased, condition to surround implanted device 300, as shown in FIG. 8B. FIG. 8B illustrates engagement subassembly 930 including at least three capture members 93, each of which includes an elongate spring-biased wire and a grip 931 that is located between a proximal portion 932P of the wire and a distal portion 932D of the wire. Capture members 93 are shown arranged around, and spring biased outward from, a longitudinal axis 9 of engagement subassembly 930, which becomes approximately aligned with a longitudinal axis 8 of device receptacle 830, when subassembly 930 is contained therein, as shown in FIG. 8C. With reference to FIG. 8C, receptacle 830 is sized to contain medical device 300 together with engagement subassembly 930 in a compressed condition, and has a distal-most opening 803 that allows passage of subassembly 930 and device 300 therethrough, for example, when the outer assembly of catheter 800 is advanced relative to the inner assembly of catheter 800 to retrieve device 300, as shown in FIG. 8C. According to the illustrated embodiment, each grip 931 of engagement subassembly 930 is configured to interlock with gap G (FIG. 3) between device attachment feature 310 and proximal end 381 of device housing 380, thereby engaging attachment feature 310, when device receptacle 830 forces capture members 93, against the spring-bias thereof, together toward axis 9. An exemplary configuration of grips 931 is described below. Furthermore, a length of each spring-biased wire distal portion 932D is approximately equal to a length of device housing 380, and distal portions 932D are preferably tethered together, for example, by a flexible polymer loop 933 (e.g., a polyester fiber having a fluoropolymer coating, such as PTFE), to create a distal-most opening into an adequately sized funnel-shaped interior 935 of the expanded engagement subassembly 930 (in the spring-biased condition) that can overcome the misalignment difficulty described above in conjunction with FIGS. 4A-B by surrounding implanted device 300. A maximum diameter of loop 933 may be approximately 1 inch. Once the expanded engagement assembly 930 is positioned around the implanted device, for example, as shown in FIG. 8B, the outer assembly of catheter 800 can be advanced relative to the inner assembly to force capture members 93 towards axis 9 so that grips 931 engage device attachment feature 310; then, a pull force can be applied to catheter 800, to disengage device fixation member 350 from the implant site and bring device 300 into receptacle 830, so that fingers 35 of fixation member 350 are held in the extended condition, as illustrated in FIG. 8C.

Figure 8D:
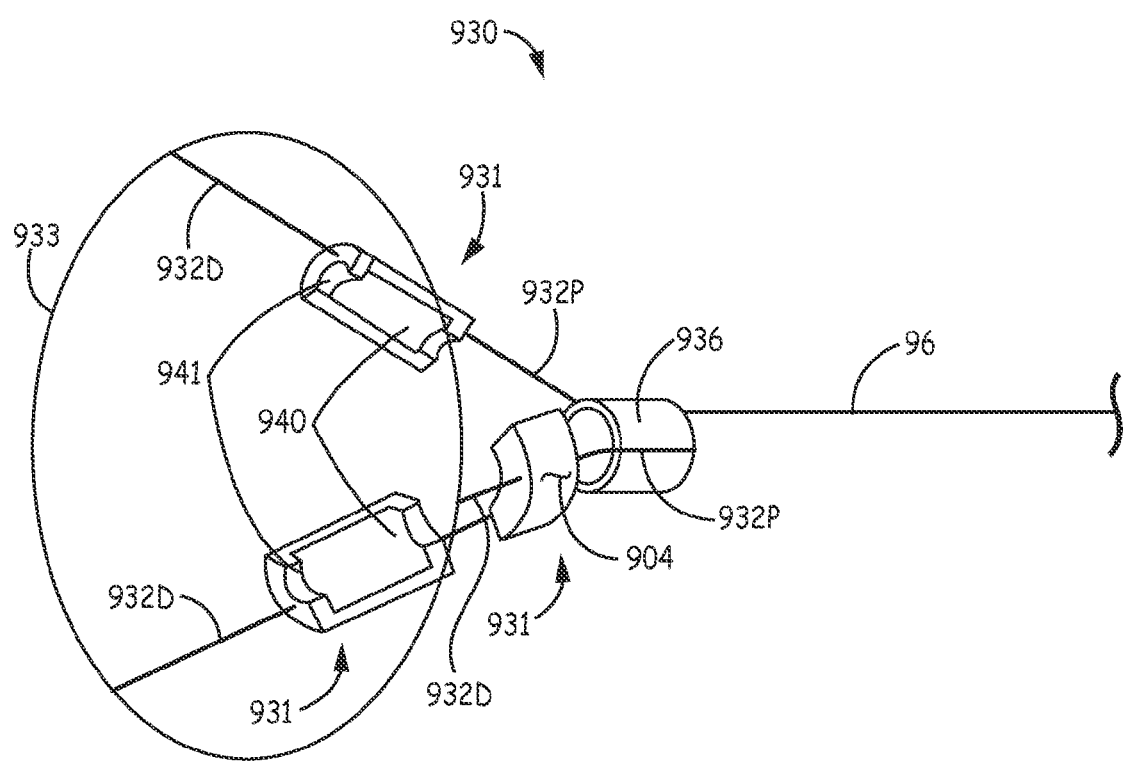
FIG. 8D is a perspective view of an engagement subassembly of the catheter of FIGS. 8A-C, according to some embodiments.

Each spring-biased wire of engagement subassembly 930 may be formed from a medical grade Stainless Steel or Nitinol wire that has a diameter of approximately 0.010 inch, although elliptical or square profile wire may be employed. Each grip 931 of subassembly 930 is preferably formed from a relatively hard medical grade plastic, such as a PEBAX® that has a durometer of about 72 D, and may be insert molded around, or otherwise secured to the corresponding wire between proximal and distal portions 932P, 932D. Proximal portions 932D of the wires may be secured to distal end of inner assembly shaft 910, for example, by welding and/or crimping according to methods known in the art. With reference to FIG. 8D, which is a perspective view of engagement subassembly 930, according to some embodiments, each grip 931 includes an inner cavity 940 recessed from a distal shoulder 941, wherein cavity 940 provides clearance for device attachment feature 310 when shoulder 941 interlocks with gap G between device attachment feature 310 and device housing proximal end 381. FIG. 8D further illustrates an outer surface 904 of each grip 931 having a curved contour that generally conforms to an inner surface of device receptacle 830.

With further reference to FIG. 8D, according to some preferred embodiments, engagement subassembly 930 further includes an elongate pull wire 96 and a corresponding a pull band 936, to which wire proximal portions 932P are coupled and to which a distal end of pull wire 96 is coupled, for example, by welds and/or crimps. In these embodiments, pull band 936 is mounted in the distal end of inner assembly shaft 910, and pull wire 96 extends proximally therefrom within shaft 910. Pull band 936 may have an outer diameter of approximately 0.120 inch. With reference to FIG. 8A, in these embodiments, another control member 854 of handle 850, which is coupled to a proximal end of pull wire 96, can be moved per arrow F, to deflect the inner assembly of catheter 800. When engagement assembly 930 is contained within device receptacle 830, the deflection of the inner assembly may also cause the outer assembly to deflect, which can help an operator to steer catheter into proximity with implanted device 300; and, after the outer assembly is retracted relative to the inner assembly, the deflection of the inner assembly can help the operator to adjust a position of the expanded engagement assembly 930 for better alignment with the implanted device 300.

FIG. 9A is a plan view of a portion of an interventional medical system that includes a catheter 8000, according to yet further embodiments; and FIG. 9B is another plan view of the system, with a partial cross-section. Catheter 8000 is shown including the same outer assembly as catheter 800, but an inner assembly of catheter 8000 is shown including an engagement subassembly 130 in lieu of engagement subassembly 930. FIGS. 9A-B illustrate engagement subassembly 130, like subassembly 930, being coupled to the distal end of inner assembly shaft 910, and being in sliding engagement with device receptacle 830 of the outer assembly. Also, like subassembly 930, engagement subassembly 130 includes at least three capture members 13 arranged around and spring-biased outward from a longitudinal axis 1 of subassembly 130; but, in contrast to subassembly 930, a grip 131 of each capture member 13 of subassembly 130, which is configured to interlock with gap G between device attachment feature 310 and proximal end 381 of device housing 380, for example, as shown in FIG. 9B, is integrally formed with a elongate spring-biased wire of the corresponding capture member 13. Each spring-biased wire of engagement subassembly 130 may be formed from a medical grade Stainless Steel or Nitinol wire that has a diameter of approximately 0.010 inch, although elliptical or square profile wire may be employed. With further reference to FIGS. 9A-B, a pre-formed intermediate portion of the spring-biased wire of each capture member 13, which is located between a wire proximal portion 132P and a wire distal portion 132D, forms grip 131.

Like distal portions 932D of the spring-biased wires of engagement subassembly 930, distal portions 132D of the spring-biased wires of engagement subassembly 130 have a length approximately equal to that of device housing 380, so that, when the outer assembly of catheter 8000 is retracted relatively to the inner assembly, as shown in FIG. 9A, a funnel-shaped interior 135 of the expanded engagement subassembly 130 is adequately sized to surround the implanted device 300. FIG. 9A further illustrates wire distal portions 132D of engagement subassembly 130 being tethered together by polymer loop 933, which forms a distal-most opening into interior 135 of the expanded engagement subassembly 130, and may have a maximum diameter of approximately 1 inch. After expanded subassembly 130 is positioned to surround the implanted device 300, the outer assembly of catheter 8000 can be advanced over subassembly 130 to force capture members 13 toward axis 1, so that grips 131 interlock with gap G, and wire distal portions 132D extend alongside device housing 380; then, a pull force can be applied to catheter 8000 to disengage device fixation member 350 from the implant site and bring device 300 into receptacle 830, so that fingers 35 of fixation member 350 are held in the extended condition, as illustrated in FIG. 9B. Although not shown, subassembly 130 may include the above-described elongate pull wire 96 coupled to pull band 936, wherein wire proximal portions 132P are also coupled to pull band 936, similar to subassembly 930.

In the foregoing detailed description, the invention has been described with reference to specific embodiments. However, it may be appreciated that various modifications and changes can be made without departing from the scope of the invention as set forth in the appended claims.

For example, the following Items are illustrative of further embodiments: Item 1. An interventional medical system comprising an implantable medical device and a catheter; the medical device comprising an electronic controller, a hermetically sealed housing containing the controller, an electrode electrically coupled to the controller and mounted in proximity to a distal end of the housing, an attachment feature joined to a proximal end of the housing and protruding proximally therefrom, and a fixation member mounted to the distal end of the housing; the catheter comprising an inner assembly and an outer assembly; the catheter outer assembly comprising an elongate shaft and a device receptacle joined to a distal end of the shaft, the shaft including a longitudinally extending lumen, the device receptacle being sized to contain the medical device therein and having a distal-most opening that allows passage of the medical device therethrough, the device receptacle being in fluid communication with the shaft lumen, and the device receptacle having a longitudinal axis extending from the shaft lumen to the distal-most opening; the catheter inner assembly comprising an elongate shaft and an engagement subassembly coupled to a distal end of the inner assembly shaft, the inner assembly shaft being in sliding engagement with the lumen of the outer assembly shaft, and the engagement subassembly being in sliding engagement with the outer assembly receptacle and having a longitudinal axis approximately aligned with the longitudinal axis of the device receptacle, when contained therein, the engagement subassembly including at least three capture members arranged around the longitudinal axis of the engagement subassembly and being spring biased outward from the longitudinal axis thereof, each capture member comprising an elongate spring-biased wire, and each wire including a proximal portion and a distal portion; and an improvement to each capture member of the engagement subassembly comprising:
- a grip located between the proximal and distal portions of the corresponding spring-biased wire, the grip being configured to interlock within a gap between the device attachment feature and the proximal end of the device housing, when the device receptacle of the catheter outer assembly forces the capture members, against the spring-bias thereof, toward the longitudinal axis of the engagement subassembly; and
a length of the distal portion of each spring-biased wire approximately equal to a length of the device housing, each distal portion extending alongside the device housing when the grip of each capture member interlocks within the gap between the device attachment feature and the proximal end of the device housing.

Item 2. The system of item 1, wherein the grip of each capture member of the engagement subassembly comprises a polymer component secured to the corresponding spring-biased wire.

Item 3. The system of any one of items 1-2, wherein the grip of each capture member of the engagement subassembly comprises a pre-formed intermediate portion of the spring-biased wire.

Item 4. The system of any one of items 1-3, wherein the engagement subassembly further comprises a flexible polymer loop secured to the distal portion the spring-biased wire of each capture member, the loop defining a distal-most opening into an interior of the engagement subassembly.

Item 5. The system of any one of items 1-4, wherein the engagement subassembly further comprises a pull band and an elongate pull wire coupled thereto, the pull wire extending along a length of the inner assembly shaft, the proximal portion of the spring-biased wire of each capture member being coupled to the pull band, and the pull band being mounted in the distal end of the inner assembly shaft.

Item 6. A catheter for retrieving an implantable medical device from an implant site, the catheter comprising an inner assembly and an outer assembly; the catheter outer assembly comprising an elongate shaft and a device receptacle joined to a distal end of the shaft, the shaft including a longitudinally extending lumen, the device receptacle being sized to contain the medical device therein and having a distal-most opening that allows passage of the medical device therethrough, the device receptacle being in fluid communication with the shaft lumen, and the device receptacle having a longitudinal axis extending from the shaft lumen to the distal-most opening; the catheter inner assembly comprising an elongate shaft and an engagement subassembly coupled to a distal end of the inner assembly shaft, the inner assembly shaft being in sliding engagement with the lumen of the outer assembly shaft, and the engagement subassembly being in sliding engagement with the outer assembly receptacle and having a longitudinal axis approximately aligned with the longitudinal axis of the device receptacle, when contained therein, the engagement subassembly including at least three capture members arranged around the longitudinal axis of the engagement subassembly and being spring biased outward from the longitudinal axis thereof, each capture member comprising an elongate spring-biased wire, and each wire including a proximal portion and a distal portion; and an improvement to each capture member of the engagement subassembly comprising:
- a grip located between the proximal and distal portions of the corresponding spring-biased wire, the grip being configured to interlock within a gap between an attachment feature of the device and a proximal end of a housing of the device, when the device receptacle of the catheter outer assembly forces the capture members, against the spring-bias thereof, toward the longitudinal axis of the engagement subassembly; and
- a length of the distal portion of each spring-biased wire approximately equal to a length of the housing of the device, each distal portion extending alongside the device housing when the grip of each capture member interlocks within the gap between the device attachment feature and the proximal end of the device housing.

Item 7. The catheter of item 6, wherein the grip of each capture member of the engagement subassembly comprises a polymer component secured to the corresponding spring-biased wire.

Item 8. The catheter of any one of items 6-7, wherein the grip of each capture member of the engagement subassembly comprises a pre-formed intermediate portion of the spring-biased wire.

Item 9. The catheter of any one of items 6-8, wherein the engagement subassembly further comprises a flexible polymer loop secured to the distal portion the spring-biased wire of each capture member, the loop defining a distal-most opening into an interior of the engagement subassembly.

Item 10. The catheter of any one of items 6-9, wherein the engagement subassembly further comprises a pull band and an elongate pull wire coupled thereto, for deflection of the inner assembly shaft, the pull wire extending along a length of the inner assembly shaft, the proximal portion of the spring-biased wire of each capture member being coupled to the pull band, and the pull band being mounted in the distal end of the inner assembly shaft.

Item 11. An engagement subassembly for an inner assembly of a catheter for retrieving an implanted medical device, and the subassembly comprising:
- an elongate pull wire extending from a proximal end thereof to distal end thereof over a length approximately equal to a length of a shaft of the inner assembly;
- a pull band coupled to the distal end of the pull wire and configured for mounting in a distal end of the inner assembly shaft for deflection thereof; and
- at least three capture members arranged around a longitudinal axis of the engagement subassembly and being spring biased outward from the longitudinal axis, each capture member comprising:
  - a spring-biased wire including a proximal portion and a distal portion; and
  - a grip located between the proximal and distal portions of each spring-biased wire, each grip being configured to interlock within a gap between an attachment feature of the device and a proximal end of a housing of the device, when a device receptacle of an outer assembly of the catheter forces the capture members, against the spring-bias thereof, toward the longitudinal axis of the engagement subassembly.

Item 12. The subassembly of item 11, wherein the grip of each capture member comprises a polymer component secured to the corresponding spring-biased wire.

Item 13. The subassembly of any one of items 11-12, wherein the grip of each capture member comprises a pre-formed intermediate portion of the spring-biased wire.

Item 14. The subassembly of any one of items 11-13, wherein the distal portion of each capture member extends over a length approximately equal to a length of the housing of the device.

Item 15. The subassembly of any one of items 11-14, further comprising a flexible polymer loop secured to the distal portion the spring-biased wire of each capture member, the loop defining a distal-most opening into an interior of the subassembly.

Item 16. An interventional medical system comprising an implantable medical device and a catheter; the medical device comprising an electronic controller, a hermetically sealed housing containing the controller, an electrode electrically coupled to the controller and mounted in proximity to a distal end of the housing, an attachment feature joined to a proximal end of the housing and protruding proximally therefrom, and a fixation member mounted to the distal end of the housing; the catheter comprising an inner assembly and an outer assembly; the catheter outer assembly comprising an elongate shaft and a device receptacle joined to a distal end of the shaft, the shaft including a longitudinally extending lumen, the device receptacle being sized to contain the medical device therein and having a distal-most opening that allows passage of the medical device therethrough, the device receptacle being in fluid communication with the shaft lumen, and the device receptacle having a longitudinal axis extending from the shaft lumen to the distal-most opening; the catheter inner assembly comprising an elongate shaft and an engagement subassembly coupled to a distal end of the inner assembly shaft, the inner assembly shaft being in sliding engagement with the lumen of the outer assembly shaft, the engagement subassembly being in sliding engagement with the device receptacle of the outer assembly, and having a longitudinal axis approximately aligned with the longitudinal axis of the device receptacle, when contained therein, the engagement subassembly including at least three longitudinally extending segments arranged around, and being spring biased outward from, the longitudinal axis of the subassembly, the segments defining an interior of the engagement subassembly, the interior being sized to contain the attachment feature of the medical device, when the spring-biased segments are forced, against the spring bias thereof, toward the longitudinal axis of the subassembly by the device receptacle; and an improvement to each spring-biased segment of the engagement subassembly comprises:
a distal-facing surface tapering outward from the longitudinal axis of the engagement subassembly in a distal direction, the distal-facing surfaces of the segments, together, defining a distal-most opening into the interior of the engagement subassembly; and
an interlocking edge terminating the distal-facing surface at a proximal end thereof; and
wherein the distal-facing surface is oriented for confronting engagement with the proximal end of the housing of the medical device, when the device receptacle of the catheter outer assembly forces the segments, against the spring-bias thereof, toward the longitudinal axis of the engagement subassembly; and
the interlocking edge of each segment is configured to interlock within a gap between the device attachment feature and the proximal end of the device housing, when the distal-facing surface of each segment is in confronting engagement with the proximal end of the device housing.

Item 17. The system of item 16, wherein the distal facing surface of each spring-biased segment of the engagement subassembly has a curved contour that conforms to a curved contour of the proximal end of the device housing.

Item 18. The system of any one of items 16-17, wherein the interlocking edges of the spring-biased segments of the engagement subassembly, together, define a circular perimeter of the distal-most opening into the interior of the engagement subassembly.

Item 19. The system of any one of items 16-18, wherein the catheter outer assembly further comprises a steering subassembly, the steering subassembly including a pull band and an elongate pull wire coupled thereto, the pull wire extending along a length of the outer assembly shaft, and the pull band being mounted in the distal end of the outer assembly shaft.

We claim:

1. An interventional medical system, comprising:
an implantable medical device, comprising:
a hermetically sealed housing,
an attachment feature joined to a proximal end of the housing and protruding proximally therefrom, and
a fixation member mounted to the distal end of the housing; and
a catheter comprising:
an inner assembly comprising an elongate shaft and an engagement subassembly coupled to a distal end of the inner assembly shaft, and
an outer assembly comprising a shaft, a device receptacle sized to contain the medical device therein joined to a distal end of the outer assembly shaft, the device receptacle being in fluid communication with a lumen of the outer assembly shaft and having a distal-most opening that allows passage of the medical device therethrough, wherein the inner assembly shaft is in sliding engagement with the lumen of the outer assembly shaft, and the engagement subassembly is in sliding engagement with the device receptacle and the engagement subassembly includes at least three capture members formed in a spring-biased outward relationship to a longitudinal axis thereof, wherein each capture member comprises:
an elongate spring-biased wire, and each wire includes a proximal portion and a distal portion,
a grip located between the proximal and distal portions of the corresponding spring-biased wire, the grip being configured to interlock within a gap between the device attachment feature and the proximal end of the device housing, when the device receptacle of the catheter outer assembly forces the capture members, against the spring-bias thereof, toward the longitudinal axis of the engagement subassembly, and
a length of the distal portion of each spring-biased wire being approximately equal to a length of the device housing, each distal portion extending alongside the device housing when the grip of each capture member interlocks within the gap between the device attachment feature and the proximal end of the device housing.

2. The system of claim 1, wherein the grip of each capture member of the engagement subassembly comprises a polymer component secured to the corresponding spring-biased wire.

3. The system of claim 1, wherein the grip of each capture member of the engagement subassembly comprises a pre-formed intermediate portion of the spring-biased wire.

4. The system of claim 1, wherein the engagement subassembly further comprises a flexible polymer loop secured to the distal portion the spring-biased wire of each capture member, the loop defining a distal-most opening into an interior of the engagement subassembly.

5. The system of claim 1, wherein the engagement subassembly further comprises a pull band and an elongate pull wire coupled thereto, the pull wire extending along a length of the inner assembly shaft, the proximal portion of the spring-biased wire of each capture member being coupled to the pull band, and the pull band being mounted in the distal end of the inner assembly shaft.

6. A catheter for retrieving an implantable medical device from an implant site, the medical device including a housing, the catheter comprising:
an inner assembly comprising an elongate shaft and an engagement subassembly coupled to a distal end of the inner assembly shaft, and
an outer assembly comprising a shaft, a device receptacle sized to contain the medical device therein joined to a distal end of the outer assembly shaft, the device receptacle being in fluid communication with a lumen of the outer assembly shaft and having a distal-most opening that allows passage of the medical device therethrough, wherein the inner assembly shaft is in sliding engagement with the lumen of the outer assembly shaft, and the engagement subassembly is in sliding engagement with the outer assembly receptacle and the engagement subassembly includes at least three capture members formed in a spring biased outward relationship to a longitudinal axis thereof, wherein each capture member comprises:
an elongate spring-biased wire, and each wire includes a proximal portion and a distal portion,
a grip located between the proximal and distal portions of the corresponding spring-biased wire, the grip being configured to interlock within a gap between an attachment feature of the device and a proximal end of the housing of the device, when the device receptacle of the catheter outer assembly forces the capture members, against the spring-bias thereof, toward the longitudinal axis of the engagement subassembly, and
a length of the distal portion of each spring-biased wire being approximately equal to a length of the housing of the device, each distal portion being configured to extend alongside the device housing when the grip of each capture member interlocks within the gap between the device attachment feature and the proximal end of the device housing.

7. The catheter of claim 6, wherein the grip of each capture member of the engagement subassembly comprises a polymer component secured to the corresponding spring-biased wire.

8. The catheter of claim 6, wherein the grip of each capture member of the engagement subassembly comprises a pre-formed intermediate portion of the spring-biased wire.

9. The catheter of claim 6, wherein the engagement subassembly further comprises a flexible polymer loop secured to the distal portion the spring-biased wire of each capture member, the loop defining a distal-most opening into an interior of the engagement subassembly.

10. The catheter of claim 6, wherein the engagement subassembly further comprises a pull band and an elongate pull wire coupled thereto, for deflection of the inner assembly shaft, the pull wire extending along a length of the inner assembly shaft, the proximal portion of the spring-biased wire of each capture member being coupled to the pull band, and the pull band being mounted in the distal end of the inner assembly shaft.

11. An engagement subassembly for an inner assembly of a catheter for retrieving an implanted medical device having an attachment feature and a housing, and the subassembly comprising:
an inner assembly shaft;
an elongate pull wire extending from a proximal end thereof to distal end thereof over a length approximately equal to a length of the inner assembly shaft;
a pull band coupled to the distal end of the pull wire and configured for mounting in a distal end of the inner assembly shaft for deflection thereof; and
at least three capture members arranged around a longitudinal axis of the engagement subassembly and being spring biased outward from the longitudinal axis, each capture member comprising:
a spring-biased wire including a proximal portion and a distal portion; and
a grip located between the proximal and distal portions of each spring-biased wire, each grip being configured to interlock within a gap between the attachment feature of the medical device and a proximal end of the housing of the medical device, when a device receptacle of an outer assembly of the catheter forces the capture members, against the spring-bias thereof, toward the longitudinal axis of the engagement subassembly.

12. The subassembly of claim 11, wherein the grip of each capture member comprises a polymer component secured to the corresponding spring-biased wire.

13. The subassembly of claim 11, wherein the grip of each capture member comprises a pre-formed intermediate portion of the spring-biased wire.

14. The subassembly of claim 11, wherein the distal portion of each capture member is extendable over a length approximately equal to a length of the housing of the device.

15. The subassembly of claim 11, further comprising a flexible polymer loop secured to the distal portion the spring-biased wire of each capture member, the loop defining a distal-most opening into an interior of the subassembly.

16. An interventional medical system comprising an implantable medical device, comprising:
a hermetically sealed housing,
an attachment feature joined to a proximal end of the housing and protruding proximally therefrom, and
a fixation member mounted to the distal end of the housing; and
a catheter comprising:
an inner assembly comprising an elongate shaft and an engagement subassembly coupled to a distal end of the inner assembly shaft, and
an outer assembly comprising a shaft, a device receptacle sized to contain the medical device therein joined to a distal end of the outer assembly shaft, the device receptacle being in fluid communication with a lumen of the outer assembly shaft and having a distal-most opening that allows passage of the medical device therethrough, wherein the inner assembly shaft is in sliding engagement with the lumen of the outer assembly shaft, the engagement subassembly being in sliding engagement with the device receptacle of the outer assembly, and having a longitudinal axis approximately aligned with the longitudinal axis of the device receptacle, when contained therein, the engagement subassembly including at least three longitudinally extending segments arranged around, and being spring biased outward from, the longitudinal axis of the subassembly, the segments defining an interior of the engagement subassembly, the interior being sized to contain the attachment feature of the medical device, when the spring-biased segments are forced, against the spring bias thereof, toward the longitudinal axis of the subassembly by the device receptacle; wherein each spring-biased segment of the engagement subassembly comprises:

a distal-facing surface tapering outward from the longitudinal axis of the engagement subassembly in a distal direction, the distal-facing surfaces of the segments, together, defining a distal-most opening into the interior of the engagement subassembly; and an interlocking edge terminating the distal-facing surface at a proximal end thereof; and wherein the distal-facing surface is oriented for confronting engagement with the proximal end of the housing of the medical device, when the device receptacle of the catheter outer assembly forces the segments, against the spring-bias thereof, toward the longitudinal axis of the engagement subassembly; and the interlocking edge of each segment is configured to interlock within a gap between the device attachment feature and the proximal end of the device housing, when the distal-facing surface of each segment is in confronting engagement with the proximal end of the device housing.

17. The system of claim 16, wherein the distal facing surface of each spring-biased segment of the engagement subassembly has a curved contour that conforms to a curved contour of the proximal end of the device housing.

18. The system of claim 16, wherein the interlocking edges of the spring-biased segments of the engagement subassembly, together, define a circular perimeter of the distal-most opening into the interior of the engagement subassembly.

19. The system of claim 16, wherein the catheter outer assembly further comprises a steering subassembly, the steering subassembly including a pull band and an elongate pull wire coupled thereto, the pull wire extending along a length of the outer assembly shaft, and the pull band being mounted in the distal end of the outer assembly shaft.

* * * * *